United States Patent
Turner et al.

(10) Patent No.: US 9,945,816 B2
(45) Date of Patent: Apr. 17, 2018

(54) ULTRASONIC NDT SENSOR ARRANGEMENT AND METHOD FOR INSPECTING SURFACES OF VARIABLE GEOMETRY OF METAL BODIES

(71) Applicant: Ansaldo Energia IP UK Limited, London OT (GB)

(72) Inventors: John Lilburne Turner, Turgi (CH); David Thomas Clarke, Warrington (GB)

(73) Assignee: ANSALDO ENERGIA IP UK LIMITED, London (GB)

(*) Notice: Subject to any disclaimer, the term of this patent is extended or adjusted under 35 U.S.C. 154(b) by 532 days.

(21) Appl. No.: 14/488,880

(22) Filed: Sep. 17, 2014

(65) Prior Publication Data
US 2015/0000408 A1    Jan. 1, 2015

Related U.S. Application Data

(63) Continuation of application No. PCT/EP2013/055804, filed on Mar. 20, 2013.

(30) Foreign Application Priority Data

Mar. 20, 2012 (EP) .................................... 12160327

(51) Int. Cl.
*G01N 29/28* (2006.01)
*G01N 29/04* (2006.01)
(Continued)

(52) U.S. Cl.
CPC ........... *G01N 29/041* (2013.01); *G01N 29/07* (2013.01); *G01N 29/226* (2013.01);
(Continued)

(58) Field of Classification Search
CPC .... G01N 29/041; G01N 29/07; G01N 29/226; G01N 29/2487; G01N 29/266; G01N 29/28
See application file for complete search history.

(56) References Cited

U.S. PATENT DOCUMENTS 3,550,438 A    12/1970    Kapluszak
3,631,714 A *    1/1972    Cressman ............ G01N 29/265
                                                                          73/641
(Continued)

FOREIGN PATENT DOCUMENTS

EP        0 359 546 A2    3/1990
EP        0359546 A2    3/1990
(Continued)

OTHER PUBLICATIONS

Office Action for European Patent Application Serial No. 13 710 435.2 dated Oct. 20, 2017.

*Primary Examiner* — Helen Kwok
(74) *Attorney, Agent, or Firm* — Buchanan Ingersoll & Rooney PC

(57) ABSTRACT

The invention relates to an ultrasonic NDT sensor arrangement for inspecting surfaces of variable geometry of metal bodies. The sensor arrangement includes a housing with a hollow inner space and an opening, through which part of an incoming sound beam exits the housing to enter a metal body to be tested. An ultrasonic sensor is coupled to the housing such that it emits said incoming sound beam directly into said hollow inner space in a direction towards the opening. The said inner space of the housing is filled with a first coupling fluid which is water. The opening of the housing is closed with a closing member, which is made of a silicone material and which has a similar density and velocity of sound compared to the first coupling fluid.

20 Claims, 2 Drawing Sheets

(51) Int. Cl.
  *G01N 29/22* (2006.01)
  *G01N 29/24* (2006.01)
  *G01N 29/265* (2006.01)
  *G01N 29/07* (2006.01)
  *G10K 11/02* (2006.01)

(52) U.S. Cl.
  CPC ....... *G01N 29/2487* (2013.01); *G01N 29/265* (2013.01); *G01N 29/28* (2013.01); *G01N 2291/011* (2013.01); *G01N 2291/0234* (2013.01); *G01N 2291/0289* (2013.01); *G01N 2291/044* (2013.01); *G01N 2291/101* (2013.01); *G01N 2291/2638* (2013.01); *G10K 11/02* (2013.01)

(56) References Cited

U.S. PATENT DOCUMENTS

| | | | | |
|---|---|---|---|---|
| 4,059,098 A * | 11/1977 | Murdock | ............ | A61B 8/4281 600/437 |
| 4,120,291 A * | 10/1978 | Paton | ............ | A61B 8/00 73/618 |
| 4,181,120 A * | 1/1980 | Kunii | ............ | G10K 11/355 600/459 |
| 4,208,917 A * | 6/1980 | Aoyama | ............ | G01N 29/221 73/588 |
| 4,211,949 A * | 7/1980 | Brisken | ............ | G10K 11/02 310/322 |
| 4,246,791 A | 1/1981 | Glenn | | |
| 4,300,217 A * | 11/1981 | Ballinger | ............ | G10K 11/002 181/139 |
| 4,545,385 A * | 10/1985 | Pirschel | ............ | A61B 8/0825 128/915 |
| 4,612,809 A * | 9/1986 | Cribbs | ............ | G01N 29/262 600/437 |
| 4,867,169 A * | 9/1989 | Machida | ............ | G10K 11/02 600/446 |
| 4,901,729 A * | 2/1990 | Saitoh | ............ | G10K 11/02 310/336 |
| 4,977,780 A * | 12/1990 | Machida | ............ | G10K 11/02 600/459 |
| 5,426,980 A * | 6/1995 | Smith | ............ | G01N 29/069 73/632 |
| 5,602,336 A * | 2/1997 | Takeuchi | ............ | G01N 29/043 73/619 |
| 6,047,603 A * | 4/2000 | Ohtera | ............ | G10K 9/122 310/322 |
| 8,087,298 B1 * | 1/2012 | DiMambro | ............ | G01N 29/226 73/629 |
| 8,683,882 B2 * | 4/2014 | Jackson | ............ | G01N 29/24 73/633 |
| 2005/0126293 A1 * | 6/2005 | Dasch | ............ | G01N 29/225 73/618 |
| 2007/0144263 A1 * | 6/2007 | Fei | ............ | G01N 29/043 73/644 |
| 2007/0175282 A1 * | 8/2007 | Fetzer | ............ | G01N 29/223 73/649 |
| 2009/0301203 A1 * | 12/2009 | Brussieux | ............ | G01N 29/225 73/627 |
| 2010/0107768 A1 * | 5/2010 | Elze | ............ | G01N 29/043 73/627 |
| 2011/0000299 A1 * | 1/2011 | Isobe | ............ | G01N 29/221 73/625 |
| 2011/0072905 A1 | 3/2011 | Lam et al. | | |
| 2011/0100128 A1 * | 5/2011 | Bond-Thorley | ............ | G01N 29/28 73/641 |
| 2011/0226063 A1 * | 9/2011 | Gysling | ............ | G01F 1/66 73/623 |
| 2011/0303013 A1 * | 12/2011 | Kass | ............ | G01N 29/28 73/632 |
| 2012/0060609 A1 * | 3/2012 | Fukutomi | ............ | G01N 29/225 73/592 |
| 2012/0137779 A1 * | 6/2012 | Graff | ............ | G01N 29/2487 73/632 |
| 2013/0030727 A1 * | 1/2013 | Zalameda | ............ | G01N 29/045 702/56 |
| 2013/0074601 A1 * | 3/2013 | Jackson | ............ | G01N 29/24 73/593 |
| 2013/0074602 A1 * | 3/2013 | Jackson | ............ | G01N 29/28 73/633 |
| 2014/0007689 A1 * | 1/2014 | Bond-Thorley | ... | G01N 29/2493 73/618 |

FOREIGN PATENT DOCUMENTS

| | | |
|---|---|---|
| GB | 2 197 474 A | 5/1988 |
| GB | 2197474 A | 5/1988 |
| JP | H10267903 A | 10/1998 |

* cited by examiner

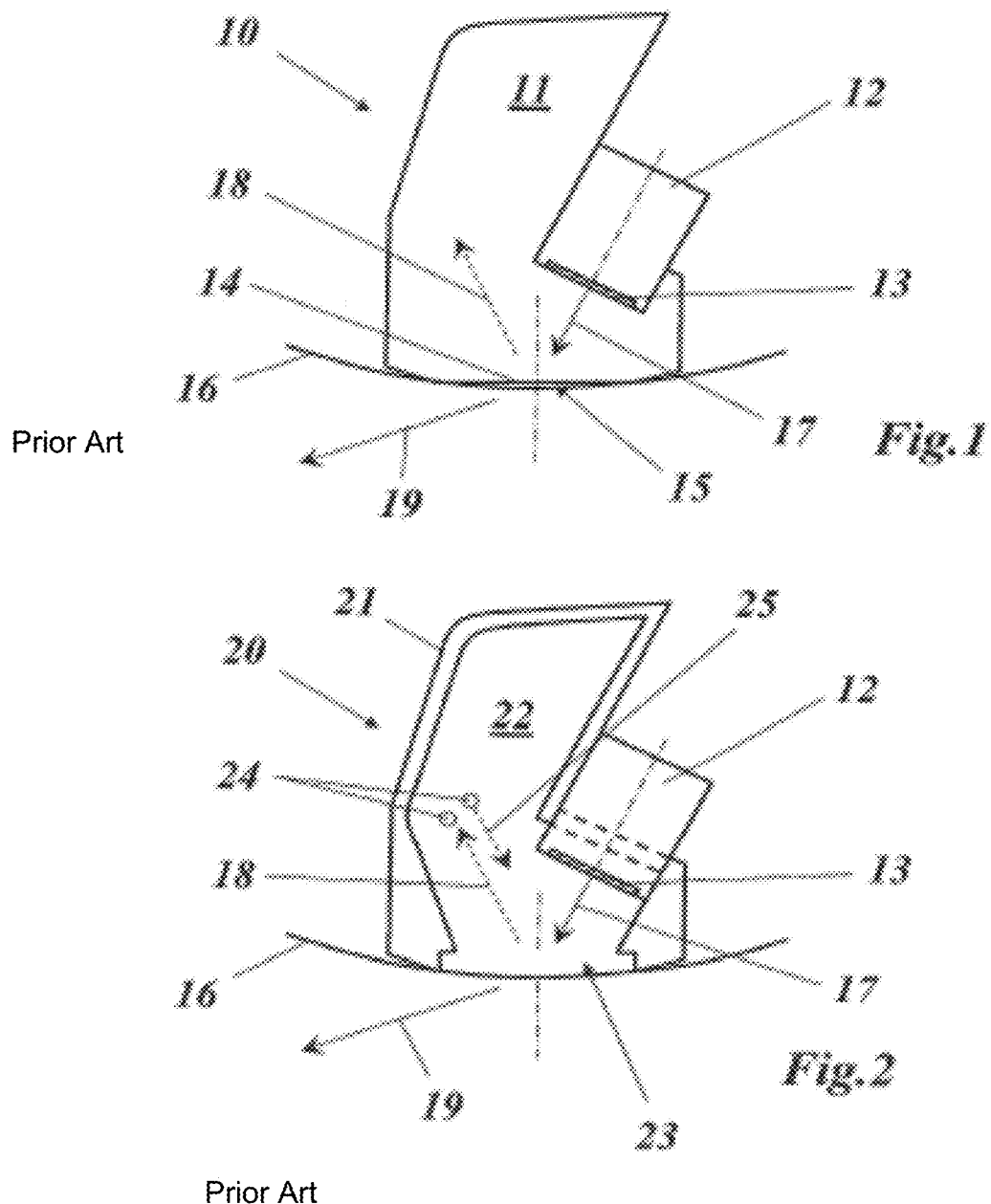

ULTRASONIC NDT SENSOR ARRANGEMENT AND METHOD FOR INSPECTING SURFACES OF VARIABLE GEOMETRY OF METAL BODIES

CROSS-REFERENCE TO RELATED APPLICATIONS

This application claims priority to PCT/EP2013/055804 filed Mar. 20, 2013, which claims priority to European application 12160327.8 filed Mar. 20, 2012, both of which are hereby incorporated in their entireties.

TECHNICAL FIELD

The present invention relates to the non-destructive testing (NDT) of metal bodies, for example, gas turbines or similar. It refers to an ultrasonic NDT sensor arrangement and a method for inspecting surfaces of variable geometry of metal bodies.

Especially, the invention describes a technique used to couple an ultrasonic sensor to a surface of variable geometry for the purpose of maintaining contact during an ultrasonic inspection, in which the transducer is continuously moved along the surface.

BACKGROUND

FIG. 1 shows in a simplified schematic diagram an ultrasonic sensor 12 positioned above a surface 16 of variable geometry of a metal body to be tested. The sensor 12 is supported a plastic wedge 11 so that it can send a projected sound beam 19 into the metal body below it at the desired angle to the surface 16. The projected sound beam 19 is part of an incoming sound beam 17 emanating from a piezoelectric element 13 within said ultrasonic sensor 12. Another part of said incoming sound beam 17 is reflected back at the contacting surface 14 of the wedge 11 as a scattered sound beam 18.

An ultrasonic sensor 12 of this type usually operates using the ultrasonic pulse-echo technique, in which a pulse of ultrasound (usually in the range 1 to 25 MHz) is projected into the material under test. When a defect is situated in the path of the sound beam, some of the sound energy (the "echo") is reflected by the defect and returns to the sensor, with the travel time being used to give an indication of the distance of the defect from the sensor 12.

However, if the wedge 11 that supports the sensor 12 has to be machined with a fixed curvature, it is hard to fill the gap 15 between the contacting surface 14 of the plastic wedge 11 and a changing surface 16 with an acoustically compatible liquid. Thus the performance of the sensor arrangement 10 under these conditions is unpredictable.

The first attempt to improve the situation was (see FIG. 2) to manufacture a sensor arrangement 20 with a hollow housing 21 for the sensor 12, fill its inner space 22 with water and let the incoming sound beam 17 travel from the sensor 12 directly through the water into the material via surface 16. This was a definite improvement over the plastic wedge 11, but caused other problems, such as (i) the need to continuously pump water through the housing 21 to maintain the coupling and (ii) the ultrasonic noise generated by sound waves scattered from air bubbles 24 brought in by the water (scattered sound 25). So a solution had to be found to circumvent these difficulties.

In the prior art, document U.S. Pat. No. 3,550,438 discloses an ultrasonic inspection apparatus, which includes an electro-acoustic transducer, means for directing a column of water or other liquid normally to the surface of an article under inspection and at least one curved reflecting surface to reflect an ultrasonic beam emitted by the transducer and to concentrate the reflected beam on a region where the liquid column strikes the surface of the article. The apparatus is for inspecting a hot article and the liquid strikes the article at sufficient speed to prevent the liquid reaching boiling point where the column strikes the surface, while also acting as a coupling liquid. The apparatus is designed for inspection of a continuous cast billet of axisymmetric geometry, whereas the invention described here will inspect components of asymmetric geometry.

On the other hand, document U.S. Pat. No. 4,246,791, which relates to the different technical field of clinical diagnosis, discloses a portable ultrasonic scanning module, which includes a fluid-tight enclosure having a window at about the front thereof and a reflective scanner at about the rear thereof and generally facing the window. A transducer is mounted in the enclosure frontwardly of the reflective scanner with the ultrasound-emitting face of the transducer generally facing the reflective scanner and being oriented with respect to the reflective scanner at a relatively acute angle such that the beam effectively "doubles-back" past itself during its excursion through the scanning module. The module is used to produce images of the interior of the human body.

Document JP 10267903 describes a solution to reduce a multiecho and also to improve the accuracy of a flaw detection result in the inspection of a specimen with an ultrasonic wave, by forming an ultrasonic transfer part with polyethylene resin having an acoustic impedance of at most twice the acoustic impedance of an acoustic coupling medium. Within the disclosed solution water is used as an acoustic coupling medium. A longitudinal wave excited by an oscillator is propagated in a wedge, and reflected and refracted at a boundary surface. Then the transmitted longitudinal wave is propagated in the acoustic coupling medium. Where the ultrasonic wave is made incident from the water to acrylic resin, 37% of the sound pressure is reflected. In the case from the water to polyethylene resin, only 8.36% of the sound pressure is reflected, and therefore the level of the reflected wave is reduced.

Document EP 0 359 546 A2 discloses an ultrasonic scanning probe comprising a coupling fluid interposed between a transducer and a probe window, characterized in that said coupling fluid comprises a mixture of 1-Butanol and Glycerol. Document GB 2197 474 A discloses an acoustic borehole imaging tool with a lubrication fluid as internal fluid. Document U.S. Pat. No. 4,612,809 describes an ultrasonic probe which is used for medical diagnostic apparatus. The inner fluid is a fluorocarbon with a sound velocity of about one-third of the sound velocity of water.

SUMMARY

It is an object of the present invention to provide an ultrasonic NDT sensor arrangement and method for inspecting surfaces of variable geometry of metal bodies, which result in substantially improved signal-to-noise ratios even in the case of changing surface contours.

This object is obtained by an ultrasonic NDT sensor arrangement and method according to claims 1 and 7.

The new and improved ultrasonic NDT sensor arrangement comprises:

a) a housing with a hollow inner space and an opening, through which part of an incoming sound beam exits the housing to enter a metal body to be tested;
b) an ultrasonic sensor coupled to said housing such that it emits said incoming sound beam directly into said hollow inner space in a direction towards said opening, whereby
c) said inner space of said housing is filled with a first coupling liquid, which is water and
d) said opening of said housing is closed with a closing member, which is made of a silicone material and which has a similar density and velocity of sound compared to water.

According to an embodiment of the invention said closing member is a membrane.

According to another embodiment of the invention said ultrasonic sensor is oriented with respect to said opening or closing member such that said part of the incoming sound beam, which exits the housing, enters said metal body at a predetermined angle to its surface.

According to another embodiment of the invention a pump is connected to the inner space of said housing to supply said sensor arrangement with said first coupling fluid.

According to another embodiment of the invention said ultrasonic sensor comprises a short-pulsed, broad-bandwidth piezoelectric element.

The method according to the invention comprises the steps of:
a) providing an ultrasonic NDT sensor arrangement according to the invention;
b) putting down said sensor arrangement with said closing member on a surface of a metal body to be tested;
c) filling a gap, which exists between said closing member and said surface of said metal body, with a film of a second coupling fluid; and
d) moving said sensor arrangement in a moving direction over said surface.

According to an embodiment of the invention water is used as said second coupling fluid.

BRIEF DESCRIPTION OF THE DRAWINGS

The present invention is now to be explained more closely by means of different embodiments and with reference to the attached drawings.

FIG. 1 shows in a simplified schematic diagram a sensor arrangement according to the prior art;

FIG. 2 shows in a diagram similar to FIG. 1 a sensor arrangement with a fluid-filled hollow housing being open towards the body to be inspected;

DETAILED DESCRIPTION

Figure 3:
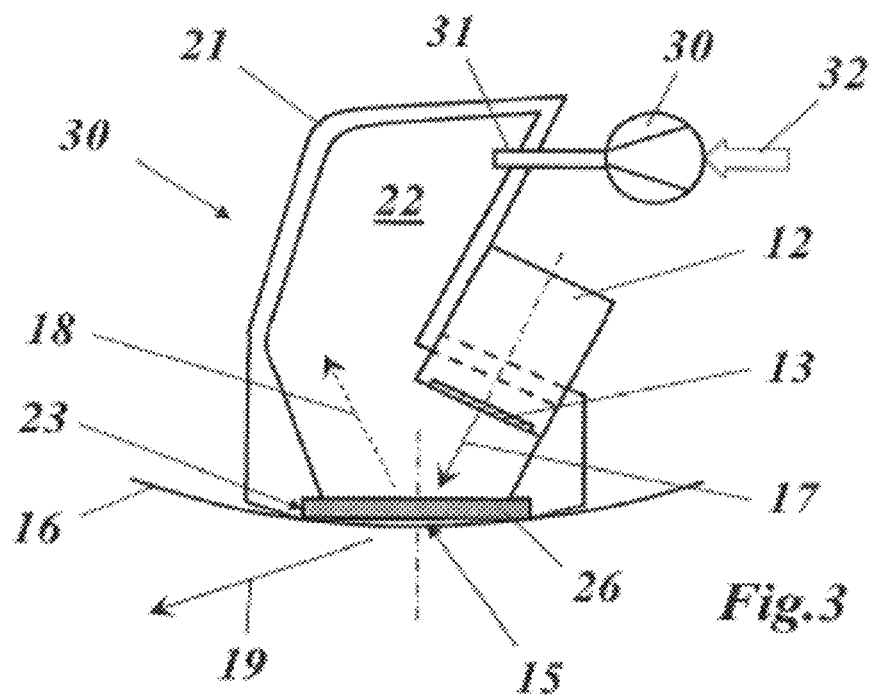
FIG. 3 shows in a diagram similar to FIG. 2 a sensor arrangement according to an embodiment of the invention.

To contain the water, which acts as a coupling fluid inside the housing 21 and to minimize the flow rate, the invention places, in a preferred embodiment, a membrane 26 of silicone material, which is acoustically compatible with water, i.e. has a similar density and velocity of sound compared to water, on the front face of the sensor (FIG. 3), thereby closing the opening 23 of the housing 21.

Because of using a membrane material 26 that is a precise acoustic match to the water within the sensor housing 21 the sound beam therefore passes through the membrane 26 in a transparent manner with no energy loss at the water-membrane interface.

Water is supplied with a pumping system (not shown). A trial was carried out on a manufactured steel test piece of variable surface geometry containing machined artificial reflectors to test the sensor's detection capabilities. There was concern that the technique would run into difficulties, since it was still necessary to provide a coupling fluid to fill the gap 27 between the membrane 26 and the steel surface 16.

However, excellent results were obtained for the reasons that are now outlined below:

There was a large reduction in the noise from air bubbles circulating inside the housing 21.

There was no loss in sensor sensitivity, since the sound beam was projected through water via an acoustically compatible material.

Figure 4:
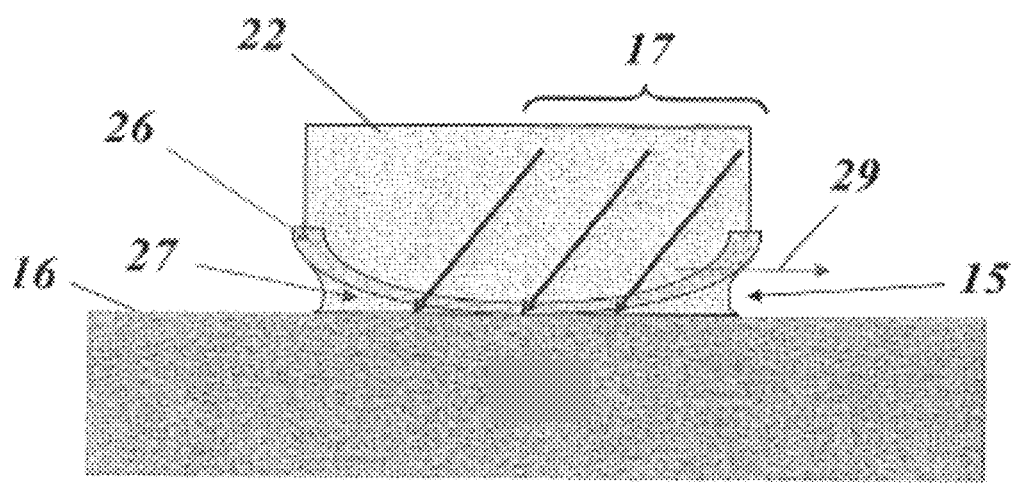
FIG. 4 shows the capillary action between a sensor arrangement according to FIG. 3 and the surface of a body to be inspected.

Under pressure from a pump 30, which pumps water from a water supply 32 through a feeding line 31 into the inner space 22 of the sensor arrangement 30, the membrane 26 appeared to bulge outwards from the sensor, thus leaving a smaller gap 15 between membrane 26 and steel for the coupling water to fill (see water film 27 in FIG. 4).

Furthermore, it is believed that there is contact between the membrane 26 and the surface 16, such that the water film 27 is carried along in a moving direction 29 with the sensor by capillary action between the membrane 26 and the steel (FIG. 4).

The bulging of the membrane 26 and the movement of water film 27 between it and the steel surface 16 underneath drastically reduced the large frictional forces previously associated with using this silicone material as an acoustic couplant.

The design of the sensor housing 21 and its mechanical support enabled the device to scan a surface of changing geometry in a stable, controlled manner. This was most important from the point of view of maintaining known ultrasonic beam characteristics in the steel.

It was possible to scan the whole of the prescribed extent of the surface at a speed of 50 mm/s or more and produce a continuous data record, even over an area where there was an abrupt change in geometry.

Most importantly, the combination of the improved coupling, the absence of air bubbles and the reduced acoustic noise resulted in much improved ultrasonic signals from the metal under test with appreciably higher signal-to-noise levels (by 20 to 30 dB or more).

The improved signal-to-noise allows one to benefit from another feature of the water-filled housing sensor design, as is described below:

The main purpose of the design is to control the passage of the ultrasonic beam (17) within the housing 21, so that one can reduce the internal echo signals returning to the sensor 12. These are echoes from the internal surfaces of the sensor that appear at fixed locations on the ultrasonic signal time-base, and these can easily be large enough to prevent the viewing of defect indication signals that occur at the same location in time.

In other ultrasonic NDT sensors, such echoes are an accepted feature of the device and always limit the near-surface inspection capability of the sensor.

Thus the housing 21 is designed so that only few (if any) internal echoes would return to the sensor within a time of about 100 µs from the entry point of the ultrasonic beam in the steel (at surface 16). The filling of the housing 21 with water has the effect of increasing this time (slow velocity of sound in water) and reducing the likely numbers of echoes (only one wave mode can travel in water, hence the internal echo pattern is simplified). The 100 µs time is equivalent to an inspection depth in steel of 50 mm or more.

This is a desirable situation rarely achieved with other ultrasonic sensors available for non-destructive testing, and has the great benefit of permitting inspection from the very surface of the material downwards. In the case of practically all other sensors designed for contact ultrasonic inspection, it is typically assumed to be impossible to inspect closer to the surface than a depth of about 2-3 mm.

The near-surface inspection capabilities are further improved by using short-pulsed, broad-bandwidth piezoelectric elements 13 in the sensor 12. These reduce the variations in ultrasonic amplitude (so-called near field fluctuations) that normally occur in the early part of an ultrasonic beam. this significantly improves the prospects for near-surface defect detection.

Such a near-surface inspection capability is of great potential importance in situations where it is essential (from a fracture mechanics viewpoint) to detect (and size) defects as near to the surface as possible.

The invention claimed is:

1. An ultrasonic non-destructive testing (NDT) sensor arrangement for inspecting surfaces of variable geometry of metal bodies, comprising:
   a housing with a hollow inner space and an opening, through which part of an incoming sound beam exits the housing to enter a metal body to be tested;
   an ultrasonic sensor coupled to said housing such that the ultrasonic sensor it emits said incoming sound beam directly into said hollow inner space in a direction towards said opening,
   said inner space of said housing being filled with a first coupling fluid,
   wherein the first coupling fluid is water and said opening of said housing is closed with a closing member, which is made of a silicone material and which has a similar density and velocity of sound compared to said first coupling fluid, and
   wherein the closing member is configured to bulge outwardly to contact a surface of the metal body to be tested.

2. The sensor arrangement according to claim 1, wherein said closing member is a silicone membrane and wherein the closing member is configured such that a film of water is formable when the closing member closes the opening of the housing such that the film is carried along in a moving direction with the ultrasonic sensor via a capillary action between the membrane and the metal body during movement of the ultrasonic sensor along the surface of the metal body.

3. The sensor arrangement according to claim 1, further comprising a pump connected to the inner space of said housing to supply said sensor arrangement with said first coupling fluid.

4. The sensor arrangement according to claim 1, wherein said ultrasonic sensor is oriented with respect to said opening or said closing member such that said part of the incoming sound beam, which exits the housing, enters said metal body at a predetermined angle to the surface of the metal body.

5. The sensor arrangement according to claim 1, wherein said ultrasonic sensor comprises a short-pulsed, broad-bandwidth piezoelectric element.

6. A method for inspecting surfaces of variable geometry of metal bodies, comprising:
   providing the ultrasonic NDT sensor arrangement according to claim 1;
   putting down said sensor arrangement with said closing member on a surface of the metal body to be tested;
   filling a gap, which exists between said closing member and said surface of said metal body, with a film of a second coupling fluid; and
   moving said sensor arrangement in a moving direction over said surface.

7. The method according to claim 6, wherein water is used as said second coupling fluid.

8. The method according to claim 6, wherein the closing member is configured to outwardly bulge to reduce frictional forces between the housing and the surface of the metal body during the moving of the sensor arrangement.

9. The method according to claim 6, wherein the closing member is configured to outwardly bulge to reduce formation of air bubbles to prevent air bubbles from circulating within the inner space of the housing during the moving of the sensor arrangement.

10. The sensor arrangement according to claim 1, wherein the closing member is configured to outwardly bulge to reduce frictional forces between the housing and the surface of the metal body.

11. The sensor arrangement according to claim 1, wherein the closing member is configured to outwardly bulge to prevent formation of air bubbles and circulation of air bubbles within the inner space of the housing during movement of the sensor arrangement along the surface of the metal body.

12. An ultrasonic non-destructive testing (NDT) sensor arrangement for inspecting surfaces of variable geometry of metal bodies, comprising:
   a housing with a hollow inner space and an opening,
   an ultrasonic sensor coupled to said housing, the ultrasonic sensor configured to emit a sound beam through the hollow inner space of the housing toward the opening to exit the housing to enter a metal body to be tested;
   the inner hollow space of the housing being filled with water;
   a closing member coupled to the housing to close the opening, the closing member being comprised of a material that has at least one acoustic property that is an acoustic match with the water, the closing member configured to bulge outwardly to contact a surface of the metal body such that a film of water between the closing member and the surface adjacent a location at which the closing member contacts the surface is carried along in a moving direction via a capillary action between the closing member and the metal body during movement of the housing along the surface of the metal body.

13. The sensor arrangement according to claim 12, wherein the closing member is configured to outwardly bulge to reduce frictional forces between the housing and the surface of the metal body during movement of the housing.

14. The sensor arrangement according to claim 13, wherein the closing member is also configured to outwardly bulge to reduce formation of air bubbles to prevent air bubbles from circulating within the inner space of the housing during movement of the housing.

15. The sensor arrangement according to claim 12, wherein said closing member is a silicone membrane that consists essentially of silicone.

16. The sensor arrangement according to claim 12, further comprising:
- a pump connected to the hollow inner space of said housing to supply said sensor arrangement with said water.

17. The sensor arrangement according to claim 12, wherein said ultrasonic sensor is oriented with respect to said opening or said closing member such that a part of the sound beam, which exits the housing, enters said metal body at a predetermined angle to the surface of the metal body.

18. The sensor arrangement according to claim 12, wherein said ultrasonic sensor comprises a piezoelectric element.

19. The sensor arrangement according to claim 18, wherein the ultrasonic sensor, the water, the housing, and the closing member are configured to prevent formation of internal echoes of the sound beam within the inner space of the housing during testing of the metal body.

20. The sensor arrangement according to claim 19, wherein the sensor arrangement is configured to inspect into a depth of 50 mm from the surface of the metal body and the material of the closing member is comprised of a silicone material.

\* \* \* \* \*